United States Patent [19]

Elson et al.

[11] Patent Number: 5,415,809

[45] Date of Patent: May 16, 1995

[54] METHOD FOR DETERMINATION OF DISSOLVED OXYGEN IN WATER

[75] Inventors: Jesse Elson, Doylestown; Michael Yoshpa, Chalfont, both of Pa.

[73] Assignee: Aquarium Pharmaceuticals, Inc., Chalfont, Pa.

[21] Appl. No.: 914,817

[22] Filed: Jul. 15, 1992

[51] Int. Cl.⁶ .............................................. G01N 7/00
[52] U.S. Cl. ..................... 252/408.1; 436/1; 436/904; 436/138; 73/19.1; 116/206
[58] Field of Search ................. 252/408.1; 436/1, 904, 436/138; 73/19.1; 116/206

[56] References Cited

U.S. PATENT DOCUMENTS

| | | | |
|---|---|---|---|
| 3,119,670 | 1/1964 | Mitchell et al. | 436/136 |
| 3,375,078 | 3/1968 | Dendy | 436/138 |
| 3,626,742 | 12/1971 | Hogan et al. | 436/116 |
| 3,634,038 | 1/1972 | Rampy | 422/56 |
| 3,663,176 | 5/1972 | Cagle et al. | 436/116 |
| 3,743,846 | 7/1973 | Matsumoto et al. | 250/474.1 |
| 3,849,070 | 11/1974 | Garza et al. | 436/122 |
| 3,997,419 | 12/1976 | Scott et al. | 204/415 |
| 4,023,934 | 5/1977 | Spinner et al. | 422/86 |
| 4,036,724 | 7/1977 | Binder et al. | 204/432 |
| 4,108,728 | 8/1978 | Spinner et al. | 435/296 |
| 4,169,811 | 10/1979 | Yoshikawa et al. | 242/55.2 |
| 4,349,509 | 9/1982 | Yoshikawa et al. | 422/57 |
| 4,442,297 | 4/1984 | Hill et al. | 549/206 |
| 4,541,987 | 9/1985 | Guadagno | 422/56 |
| 4,665,023 | 5/1987 | Deneke et al. | 435/28 |

FOREIGN PATENT DOCUMENTS

| | | |
|---|---|---|
| 54-46186 | 4/1979 | Japan . |
| 55-6212 | 1/1980 | Japan . |
| 56-98648 | 8/1981 | Japan . |
| 0918949 | 2/1963 | United Kingdom . |

OTHER PUBLICATIONS

"Water Analysis Handbook", Hach Company (1989), pp. 442-452.
Advertisement for a "Dissolved Oxygen Kit", Precision Aquarium Testing of Stuart Fla.

*Primary Examiner*—Gary Geist
*Assistant Examiner*—Valerie Fee
*Attorney, Agent, or Firm*—Panitch Schwarze Jacobs & Nadel

[57] ABSTRACT

A method for determining the concentration of dissolved oxygen in a water sample comprising the steps:
(a) providing a water sample of predetermined volume, the oxygen content of which is to be determined;
(b) mixing additives with the water sample to form a mixture, the additives comprising an oxidizable metal salt comprising a transition metal cation selected from the group consisting of scandium, titanium, vanadium, chromium, manganese, iron, cobalt, nickel and copper, and an anion selected from the group consisting of an inorganic anion and an organic anion which, with the cation, results in a water soluble oxidizable metal salt, at least one water soluble alkali metal compound selected from the group consisting of an alkali metal oxide and an alkali metal hydroxide and at least one oxidation-reduction indicator capable of a color change upon oxidation of the metal salt;
(c) preventing any substantial contact of the mixture with atmospheric oxygen; and
(d) comparing the color of the mixture to a predetermined color indicative of the concentration of dissolved oxygen in the water sample.

18 Claims, No Drawings

METHOD FOR DETERMINATION OF DISSOLVED OXYGEN IN WATER

FIELD OF THE INVENTION

The invention relates to a composition and method for determining the concentration of dissolved oxygen in water and, more particularly, wherein the composition comprises an oxidizable metal salt, at least one alkali metal compound, and at least one oxidation-reduction indicator capable of a color change upon oxidation of the metal salt.

BACKGROUND OF THE INVENTION

Water quality management is of particular concern in the cultivation of aquatic organisms for such purposes as food, recreation, education, research and hobbies. Fish and other aquatic animals require an adequate supply of oxygen in order to ensure survival. In addition, aerobic bacterial processes require an adequate supply of oxygen to convert toxic waste into nontoxic by-products. It is crucial to maintain a minimum level of dissolved oxygen in water in order to maintain this aquatic life.

When water is free of all aquatic life, at a water temperature of approximately 70° F. (21.1° C.), the dissolved oxygen level in water is approximately 9 parts per million (ppm). However, in the presence of aquatic animals and accompanying aerobic bacterial processes, the oxygen level may become insufficient to support such life. Therefore, it is desirable for aquaculturalists to have a simple, reliable method for testing the concentration of dissolved oxygen in a water sample in order to ensure an adequate concentration of dissolved oxygen for maintaining such aquatic life.

The prior art discloses various methods for determining the concentration of dissolved oxygen in water. For example, the Winkler or Iodometric method uses titration based upon the oxidizing property of dissolved oxygen to determine the concentration of dissolved oxygen in water. The electrometric method is based upon the rate of diffusion of molecular oxygen across a membrane of an electrode. However, these methods are prohibitively expensive both in terms of time and money to the home aquaculturalist as they require specialized titration equipment and solutions or membrane electrodes and complicated procedures for use.

Another prior art method for determining the concentration of dissolved oxygen in water ranging from 0 to 13.0 mg $O_2$/L uses a photometer to compare the color of a test water sample with a control sample containing a known concentration of oxygen. An ampul having a fracturable tip and containing an undisclosed reagent is immersed into a water sample. When the tip is fractured, a vacuum created within the ampul draws a predetermined volume of water into the ampul. The water and reagent are mixed within the ampul and the ampul is placed in the photometer to determine the concentration of dissolved oxygen in the water sample. In the presence of dissolved oxygen, the color of the reagent within the ampul changes from yellow to purple. The intensity of the purple color is proportional to the concentration of dissolved oxygen in the sample.

This method suffers from a number of drawbacks in terms of accuracy, convenience, and cost of use, especially since specialized equipment is needed. With regard to accuracy, the results obtained by use of a photometer are influenced by bubbles or particulate matter suspended in the water sample. The test results may also be influenced by the depth and turbulence of the water in the area from which the sample is taken, as well as temperature, light, sludge deposits, microbial action, travel time, mixing, and other factors affecting the water sample.

The prior art discloses another method which is used to determine concentrations of oxygen in water, such as boiler feedwater, ranging from 0 to 800 micrograms of oxygen per liter. This method follows substantially the same steps as the immediately preceding method except that a different reagent is used. In the presence of dissolved oxygen, the reagent color changes from yellow to blue, the depth of the blue color being proportional to the concentration of dissolved oxygen. This method suffers from the same types of drawbacks as that discussed above. Moreover, sodium hydrosulfite in the sample may reduce the oxidized form of the indicator solution and seriously interfere with the results of the test. Also, a 100,000-fold excess of hydrazine may reduce the oxidized form of the indicator solution.

Another method for determining dissolved oxygen concentration for use in aquaculture is disclosed in the prior art which involves substantially the same test procedures as those followed in the latter two aforementioned methods, except that the reagent changes color from yellow to purple in the presence of dissolved oxygen. The intensity of the purple color is proportional to the concentration of dissolved oxygen in the sample. This method suffers from similar drawbacks to those discussed above. In addition, magnesium, which is commonly present in sea water, may cause interference with the test results.

The prior art discloses a number of methods for determining the presence of oxygen in a gas.

There is disclosed in the prior art an oxygen-absorbing agent comprised of a ferrous compound, and, in a preferred embodiment, a metal powder such as a reduced iron, the composition exhibiting a color change upon absorption of oxygen.

The prior art also discloses a process for detecting the presence of oxygen in a gas by contacting the gas with a composition comprising a supported oxide of a transition metal of Group VB or VIB of the Periodic Table in a lower valence state. Oxygen present in the gas effects a color change in the composition. A process for detecting oxygen in a gas stream by contacting the gas with a reaction product formed by the reduction of an organo-transition metal compound with a metal hydride or an alkyl compound of metal of Groups IA, II, or IIIA of the Periodic Table is also disclosed in the prior art. The resulting product contains the transition metal in a lower valence state, and undergoes a color change.

The prior art discloses the use of ammoniated copper to indicate by color change the amount of oxygen in a gas mixture. A gas mixture containing oxygen is passed over a packed bed of inert particulate support material coated with ammoniated copper. The copper reacts with the oxygen to produce copper oxide or copper hydroxide, which in turn reacts with the ammonium ion to produce the blue cuprammonium ion. The length of the resultant colored stain on the coated support material is proportional to the amount of oxygen passed over the support material.

A number of methods for determining the concentration of oxygen in liquid are disclosed in the prior art.

There is disclosed in the prior art the use of a tube containing a colorimetric reagent which is partially evacuated and has a readily frangible tip. Examples of suitable colorimetric reagents include 5,5-indigo disulfonic acid and potassium thiocyanate. When the tube is fractured, a predetermined quantity of liquid is drawn into the tube. The reagent reacts with the liquid and develops a color proportional to the concentration of the material to be determined in the liquid. A product based upon this prior art is commercially available for use by fresh water and marine aquarists in which the dissolved oxygen content in a water sample is proportional to the intensity of the resulting blue color of the reagent within the ampul. An oxygen level of between 0 and 10 ppm is ascertainable upon visual comparison of the color of the reagent with a color chart.

The prior art discloses a method and means for determining the dissolved oxygen content in water based on the assertion that the amount of dissolved oxygen is inversely proportional to the iron content of the water. A color indicator containing tannic acid or other reagent capable of detecting minute quantities of ferrous iron in water changes color when the tannic acid or other reagent reacts with dissolved ferrous iron in the water.

Another prior art compound for indicating the presence of oxygen in a gas is comprised of at least one dyestuff, at least one alkaline substance selected from the group of oxides or hydroxides of alkaline earth metals, aluminum hydroxide, phosphates, carbonates, or organic acid salts of alkaline earth metals and at least one reducing agent selected from the group consisting of dithionites, ferrous compounds, reducing saccharides, and mixtures thereof.

While the prior art discloses a variety of methods for determining the dissolved oxygen concentration in liquids or gases, a simple, reliable method for determining the concentration of dissolved oxygen in a water sample capable of use by the home aquacultural enthusiast is needed.

DEFINITIONS

As used herein, an "alkali metal compound" is defined to mean any compound comprising a metal of Group IA of the Periodic Table.

As used herein, an "oxidizable metal salt" is defined to mean a salt of any metal except alkali metals (Group IA of the Periodic Table) and alkaline earth metals (Group IIA of the Periodic Table).

As used herein, "percent" or "%" is defined to mean percent by weight of the total composition, unless otherwise indicated.

The term "redox", as used herein, is defined to mean oxidation-reduction.

The term "substantial absence of atmospheric oxygen", as used herein, is defined to mean that the composition and water sample are mixed under atmospheric conditions in which the level of atmospheric oxygen does not significantly influence the color change of the oxidation-reduction indicator upon oxidation of the metal salt.

The term "substantially colorless", as used herein, is defined to mean that the oxidation-reduction indicator is without color or has a color which does not effect the color change for determining the concentration of oxygen in the sample upon oxidation of the metal salt.

SUMMARY OF THE INVENTION

According to the present invention, the above and other deficiencies of the prior art are alleviated or eliminated by a composition for determining the quantity of dissolved oxygen in water, comprising:
an oxidizable metal salt;
at least one alkali metal compound; and
at least one oxidation-reduction indicator capable of a color change upon oxidation of the metal salt.

A further aspect of the invention relates to a method for determining the concentration of dissolved oxygen in a water sample comprising the steps:

(a) providing a water sample of predetermined volume;

(b) mixing a composition with the water sample in the substantial absence of atmospheric oxygen to form a mixture, the composition comprising an oxidizable metal salt, at least one alkali metal compound and at least one oxidation-reduction indicator capable of a color change upon oxidation of the metal salt; and (c) comparing the color of the mixture to a predetermined color indicative of the concentration of dissolved oxygen in the water sample.

DETAILED DESCRIPTION OF THE PREFERRED EMBODIMENT

Generally, the present invention involves a chemical composition which, when added to a water sample, produces an electrochemical potential. The magnitude of the electrochemical potential is indicated by a color change of an oxidation-reduction indicator component of the composition. The color change is directly proportional to the concentration of dissolved oxygen in the water sample.

The present composition is superior to those of the prior art in that the individual components of the present composition need not be prepared or maintained under oxygen-free conditions prior to combination. In fact, two of the components may be combined prior to use. Even when the method is performed on a water sample, absolute absence of atmospheric oxygen is not required, as explained below.

One component of the present composition comprises an oxidizable metal salt. The oxidizable metal salt is preferably a salt of any metal except alkali metals (Group IA of the Periodic Table) and alkaline earth metals (Group IIA of the Periodic Table). The metal is preferably in its lowest oxidation state, although one of ordinary skill in the art would understand that the metal may be in any oxidation state as long as it is capable of being oxidized by oxygen to a higher oxidation state. The metal salt is also preferably colorless in the lower oxidation state so as not to interfere with any color change of the indicator when the composition is added to the water sample. Preferably the metal salt is in solid form, although one of ordinary skill in the art would understand that the metal salt may be in liquid form, such as an aqueous solution, as long as the effect of any dissolved oxygen in the water component of the aqueous solution is accounted for in the color change of the indicator when the composition is combined with the water sample.

Preferably, the oxidizable metal salt is a salt of a transition metal. The transition metal of the transition metal salt is preferably selected from the group consisting of scandium, titanium, vanadium, chromium, manganese, iron, cobalt, nickel and copper. In an alternative preferred embodiment, the transition metal salt is preferably a soluble ferrous salt. The soluble ferrous salt may be organic or inorganic. Examples of suitable oxidizable transition metal salts include ferrous sulfate, ferrous chloride, ferrous ammonium sulfate, ferrous citrate, or ferrous ethylenediaminetetraacetate. As presently preferred, the transition metal salt is ferrous ammonium sulfate, otherwise known as Mohr's salt.

Another component of the present composition comprises at least one alkali metal compound. The alkali metal compound may be selected from the group consisting of alkali hydroxides, alkali oxides, and alkali salts. Preferably, the alkali metal compound is selected from the group consisting of lithium hydroxide, sodium hydroxide, potassium hydroxide, rubidium hydroxide and cesium hydroxide. As presently preferred, the alkali metal compound is sodium hydroxide. Hydroxide forms of the alkali metal compound facilitate the oxidation reaction by raising the pH of the mixture of the composition and sample so that the mixture is basic.

The alkali metal compound is preferably used in solid form, however a liquid form, such as an aqueous solution, may be used as long as the effect of any dissolved oxygen in the water component of the aqueous solution is accounted for in the color change of the indicator when the composition is combined with the water sample.

Another component of the composition comprises at least one oxidation-reduction indicator capable of a color change upon oxidation of the transition metal salt. Preferably, the oxidation-reduction indicator is substantially colorless when the metal salt is in a lower oxidation state and is colored when the metal salt is in a higher oxidation state, although one skilled in the art would understand that the oxidation-reduction indicator need not be substantially colorless when the metal salt is in a lower oxidation state, as long as the oxidation-reduction indicator undergoes a color change when the metal salt is in a higher oxidation state. The color of the oxidation-reduction indicator changes at a specific electrochemical potential value which is characteristic for each oxidation-reduction indicator.

While the inventors do not wish to be bound by any specific theory, it is believed that the oxidation-reduction indicator is not directly involved in the oxidation reaction by which the oxidizable metal salt is elevated to a higher oxidation state. The action of the indicator is believed not to depend on the specific nature of the oxidant or reductant involved in the oxidation-reduction reaction, but upon the oxidation-reduction reaction achieving a reduction potential numerically equivalent to that at which the indicator undergoes a color change. The oxidized form of the indicator is preferably a different color than the reduced form or it may be colored in one form and colorless in another.

Preferably, the oxidation-reduction indicator is selected from the group consisting of indigo monosulfonate, phenosafranine, indigo tetrasulfonate, methylene blue, safranine O and mixtures thereof. In order to cover a broader range of possible values for reduction potential (i.e., dissolved oxygen concentration), a plurality of oxidation-reduction indicators may be combined in the present composition. Each indicator would be capable of changing color at a different reduction potential to thereby cover a broader range of dissolved oxygen concentrations than could be determined by use of a single indicator.

The reaction of the components in producing the color change is illustrated by the following exemplary consecutive reactions. One skilled in the art would understand in view of the present disclosure that different oxidizable metal salts, alkali metal compounds, and oxidation-reduction indicators may be used in accordance with the present invention other than those specifically set forth herein. In the first exemplary consecutive reactions, the oxidizable metal salt is ferrous chloride and in the second exemplary consecutive reactions, the oxidizable metal salt is ammonium ferrous sulfate. In each exemplary reaction, the alkali metal compound is sodium hydroxide and the oxidation-reduction indicator is preferably a combination of 80 weight percent methylene blue and 20 weight percent safranine O.

First example of consecutive reactions:
(a) $FeCl_2 + 2NaOH \rightarrow Fe(OH)_2 + 2NaCl$
(b) $4Fe(OH)_2 + O_2 + 2H_2O \rightarrow 4Fe(OH)_3$ Second example of consecutive reactions:
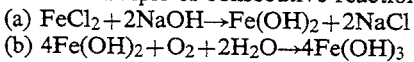
(c)  $(NH_4)_2Fe(SO_4)_2 + 4NaOH \rightarrow Fe(OH)_2 + 2NH_4OH + 2Na_2SO_4$
(d) $4Fe(OH)_2 + O_2 + 2H_2O \rightarrow 4Fe(OH)_3$ Methylene blue and safranine O are preferred because the reduction potentials at which these indicators change color corresponds to the reduction potential developed by the oxidation-reduction reaction of the preferred transition metal salt, for example, the oxidation by oxygen of a ferrous hydroxide to ferric hydroxide. For reactions such as those set forth above, the reduction potential may be calculated by the ratio of the concentration of $Fe(OH)_3$ to the concentration of $Fe(OH)_2$. The value of the reduction potential developed by the reaction depends upon the degree to which the oxygen has oxidized the ferrous form to the ferric form. Thus, the color change of the oxidation-reduction indicator depends upon the dissolved oxygen content of the water. For example, in their reduced form, both methylene blue and safranine O are colorless. However, at a reduction potential of 0.36 volts, methylene blue indicator exhibits a green-blue color. At 0.28 volts, safranine O exhibits a red color.

Table 1 provides other examples of different formulations of the composition which may be used in accordance with the present invention.

TABLE 1

| Oxidizable Metal Salt | Alkali Metal Compound | Oxidation-Reduction Indicator(s) |
|---|---|---|
| FeSO$_4$ | NaOH | Methylene Blue and Safranine O |
| FeCl$_2$ | NaOH | Methylene Blue and Safranine O |
| (NH$_4$)$_2$Fe(SO$_4$)$_2$ | NaOH | Methylene Blue and Safranine O |
| FeEDTA | NaOH | Methylene Blue and Safranine O |
| Fe Citrate | NaOH | Methylene Blue and Safranine O |

The method according to the present invention for determining the concentration of dissolved oxygen in a water sample using the present composition will now be described generally. The method generally comprises a first step of obtaining a water sample of predetermined volume, for example, 10 milliliters, in a convenient vessel, such as a test tube capable of being covered, and of such volume that there is not a considerable air space when all ingredients have been added. Thus, the test tube or other vessel should be almost completely full, so that when it is capped, the contents of the tube are in the substantial absence of atmospheric oxygen. One skilled in the art would understand that the water sample may be of any predetermined volume so long as a proportionate amount of composition is used for testing.

The method further comprises a second step of mixing the composition with the water sample in the substantial absence of atmospheric oxygen to form a mixture. The composition comprises, as discussed above, an oxidizable metal salt, at least one alkali metal compound and at least one oxidation-reduction indicator capable of undergoing a color change upon oxidation of the transition metal salt.

The components of the present composition may be in a solid or liquid state, for example in the form of powder, tablets or prepared solutions. Generally, in solid form, the oxidizable metal salt comprises about 65 to about 75, and preferably about 70 to about 73, weight percent of the composition. The alkali metal compound comprises about 20 to about 25, and preferably about 22 to about 24, weight percent of the composition. The oxidation-reduction indicator generally comprises about 1 to about 8, and preferably about 4 to about 6, weight percent of the composition.

More preferably, in solid form, the composition comprises about 1.5 milligrams of the oxidizable metal salt per milliliter of the water sample, about 0.5 milligrams of the alkali metal compound per milliliter of the water sample and about 0.1 milligrams of the oxidation-reduction indicator per milliliter of the water sample.

In liquid form, the composition preferably comprises about 0,075 milliliters of a first aqueous solution comprising about 20 percent by weight of the oxidizable metal salt, about 0.10 milliliters of a second aqueous solution comprising about 5 percent by weight of the alkali metal compound and about 0.20 milliliters of a third aqueous solution comprising about 0.5 percent by weight of the oxidation-reduction indicator per 10 milliliters of water sample. In view of the present disclosure, one skilled in the art would understand that these preferred amounts are only approximations and that these amounts may vary.

Preferably, the composition is used in the form of dry tablets. The oxidizable metal salt and oxidation-reduction indicator may be combined in a single tablet. A second tablet may contain the alkali metal compound, which, due its reactivity, generally must be kept separate from the other components of the composition until added to the water sample. Various methods of forming the tablets using conventional equipment and techniques is well within the knowledge of one skilled in the art and further discussion is therefore not believed to be necessary. The tablet form is particularly advantageous for use by the home aquaculturalist because of its simplicity and ease of handling.

The composition and sample may be mixed in a variety of ways. Preferably, a container or test tube of predetermined volume sufficient to accommodate the water sample and composition is substantially filled with the water sample. The oxidizable metal salt and indicator (in tablet form or otherwise) is added to the sample in the container and then the alkali metal compound is added. The container containing the sample and all components of the composition of the present invention is covered and the mixture may be agitated in the substantial absence of oxygen. The third step of the method may then be carried out.

The third method step is a comparison of the color of the mixture to a predetermined color indicative of the concentration of dissolved oxygen in the water sample. For example, the color of the mixture may be compared to a standard reference color chart, the colors of which have been correlated to the concentration of oxygen in parts per million with respect to each indicator or combination of indicators, thus creating a standard color comparison chart.

The use of a simple, standard, color comparison chart eliminates the need for sophisticated and costly testing equipment which is not easily adaptable to home use. Use of the present invention is not limited to the home aquaculturalist, but it may also be used in industrial and commercial applications, to name a few.

Table 2 shows the color change exhibited by the indicators methylene blue, safranine O and the preferred combination of 80 weight percent methylene blue and 20 weight percent safranine O based upon different concentrations of oxygen in test samples. The composition includes the indicator, ammonium ferrous sulfate and sodium hydroxide in the following proportions.

Approximately 15.0 milligrams of ammonium ferrous sulfate, 5.0 milligrams of sodium hydroxide and 1.0 milligram of indicator, each in solid form were added to each 10 ml water sample to form a mixture. The indicator and ammonium ferrous sulfate may be combined prior to addition to the test sample.

Each mixture was shaken and the resulting color exhibited was compared to a standard color chart, namely Pantone Color Formula Guide 747XR, 2nd Edition (1990–91), which is commercially available from Pantone, Inc. of Moonachie, N.J. However, one skilled in the art would understand that any standard color chart may be used to determine the quantity of oxygen in parts per million based upon the chosen indicator, as long as it is used consistently so that comparison standards can be established.

TABLE 2

| Concentration of Oxygen (ppm) | Methylene Blue | Safranine O | Methylene Blue and Safranine O |
| --- | --- | --- | --- |
| 0 | 317-C* | 317-C* | 317-C* |
| 2 | 317-C* | 176-C (pinkish) | 176-C (pinkish) |
| 4 | 317-C* | 177-C (pinkish) | 177-C (pinkish) |
| 6 | 284-C (blue) | 178-C (dark pink) | 2583-C (red) |
| 8 | 286-C (dark blue) | 179-C (dark red) | 2603-C (purplish) |
| 10 | 288-C (dark blue) | 180-C (dark red) | 2623-C (dark purple) |
| 12 | 484-C** | 180-C (dark red) | 175-C (dark brown) |

*Indicators (methylene blue & safranine O) are colorless, but the test sample had color 317-C (light blue) corresponding to the iron salt in solution.
**Color corresponds to that of precipitate of ferric hydroxide (brown).

Referring to Table 2, at a dissolved oxygen concentration of 0 ppm, the combined indicator of methylene blue and safranine O exhibited a light blue color corresponding to color 317-C of the Pantone chart. The color of the test sample may be attributed to the iron salt in solution and does not adversely affect the test results, which are based upon changes in color. At a dissolved oxygen content of 6 ppm, the sample exhibited a red color corresponding to color 2583-C of the Pantone chart.

The color comparison is generally not carried out until the color of the solution remains virtually unchanged. This steady state color may be achieved in as short a period of time as one minute, although one skilled in the art would understand that the time for the color change to reach steady state may vary depending on such factors as the concentration of the dissolved oxygen in the test sample and the choice of components in the composition.

The present invention is simple enough for the home aquaculturalist to employ yet meets the rigorous accuracy and precision requirements necessary to determine low concentrations of dissolved oxygen in water. The composition may be formed in a convenient solid form, such as tablets. In addition, the present method eliminates the need for expensive analysis equipment such as spectrophotometers and titrators. The present method reduces the possibility of injury to the tester since it is not necessary to the method to use an ampul (typically glass) having a fracturable tip. Therefore, the present invention fulfills a long-felt need in the art for a simple, reliable, and accurate test to determine the concentration of dissolved oxygen in a water sample.

It will be appreciated by those skilled in the art that changes could be made to the embodiments described above without departing from the broad inventive concept thereof. It is understood, therefore, that this invention is not limited to the particular embodiments disclosed, but is intended to cover modifications which are within the spirit and scope of the present invention as defined by the appended claims.

We claim:

1. A method for determining the concentration of dissolved oxygen in a liquid water sample comprising the steps:
   (a) providing a liquid water sample of predetermined volume, the oxygen content of which is to be determined;
   (b) mixing additives with the liquid water sample to form a mixture, the additives comprising an oxidizable metal salt comprising a transition metal cation selected from the group consisting of scandium, titanium, vanadium, chromium, manganese, iron, cobalt, nickel and copper, and an anion selected from the group consisting of an inorganic anion and an organic anion which, with the cation, results in a water soluble oxidizable metal salt, at least one water soluble alkali metal compound selected from the group consisting of an alkali metal oxide and an alkali metal hydroxide and at least one oxidation-reduction indicator capable of a color change upon oxidation of the metal salt during contact with dissolved oxygen in the liquid sample to a color indicative of the concentration of dissolved oxygen in the liquid sample;
   (c) preventing any substantial contact of the mixture with atmospheric oxygen; and
   (d) determining the concentration of dissolved oxygen in the liquid sample by comparing the color of the mixture to a predetermined color indicative of the concentration of dissolved oxygen in the water sample.

2. A method according to claim 1, wherein the additives are present, with respect to the total amount of additives, in amounts of about 65 to about 75 weight percent of the oxidizable metal salt in solid form, about 20 to about 25 weight percent of the alkali metal compound in solid form and about 1 to about 8 weight percent of the oxidation-reduction indicator.

3. A method according to claim 2, wherein the additives are present in amounts of about 70 to about 73 weight percent of the oxidizable metal salt, about 22 to about 24 weight percent of the alkali metal compound and about 4 to about 6 weight percent of the oxidation-reduction indicator.

4. A method according to claim 1, wherein the mixture is formed by mixing with the liquid water sample about 1.5 milligrams of the oxidizable metal salt in solid form per milliliter of the liquid water sample, about 0.5 milligrams of the alkali metal compound in solid form per milliliter of the liquid water sample, and about 0.1 milligrams of the oxidation-reduction indicator per milliliter of liquid the water sample.

5. A method according to claim 1, wherein the mixture is formed by mixing, at a concentration per about 10 milliliters of the liquid water sample, about 0.075 milliliters of a first aqueous solution comprising about 20 percent by weight oxidizable metal salt, about 0.10 milliliters of a second aqueous solution comprising about 5 percent by weight alkali metal compound and about 0.20 milliliters of a third aqueous solution comprising about 0.5 percent by weight oxidation-reduction indicator per 10 milliliters of the liquid water sample.

6. A method according to claim 1, wherein the metal salt is a soluble ferrous salt.

7. A method according to claim 6, wherein the metal salt is ammonium ferrous sulfate.

8. A method according to claim 1, wherein the alkali metal compound is selected from the group consisting of lithium hydroxide, sodium hydroxide, potassium hydroxide, rubidium hydroxide and cesium hydroxide.

9. A method according to claim 1, wherein the oxidation-reduction indicator is selected from the group consisting of indigo monosulfonate, phenosafranine, indigo tetrasulfonate, methylene blue, safranine O and mixtures thereof.

10. A method according to claim 1, wherein the oxidation-reduction indicator is substantially colorless when the metal salt is in a lower oxidation state and is colored when the metal salt is in a higher oxidation state.

11. A method according to claim 1, wherein a plurality of oxidation-reduction indicators are present, each indicator having a different color upon oxidation of the metal salt, wherein different colors indicate different concentrations of dissolved oxygen in the liquid water sample.

12. A method according to claim 1 wherein the anion is selected from the group consisting of chloride, sulfate, ammonium sulfate, citrate and ethylenediaminetetraacetate.

13. A method according to claim 1 wherein the oxidizable metal salt is in tablet form.

14. A method according to claim 1 wherein the alkali metal compound is in the form of a tablet.

15. A method according to claim 1 wherein first and second components are mixed with the liquid water sample, the first component comprising the oxidizable metal salt and the indicator, and the second component comprising the alkali metal compound.

16. A method according to claim 15 wherein each of the first and second components is in tablet form.

17. The method of claim 1 wherein the liquid water sample is representative of a body of water for which the concentration of dissolved oxygen in the body of water is to be determined.

18. A method according to claim 17 wherein the body of water is selected from the group consisting of an aquarium and a fish pond.

* * * * *